United States Patent
Burbank et al.

(10) Patent No.: US 9,485,984 B2
(45) Date of Patent: Nov. 8, 2016

(54) METHOD OF PREPARING OOCYTES, EMBRYOS, OR BLASTOCYSTS FOR CRYOPRESERVATION

(71) Applicant: Mariposa Biotechnology, Inc., San Clemente, CA (US)

(72) Inventors: Fred H. Burbank, San Clemente, CA (US); Michael L. Jones, San Clemente, CA (US)

(73) Assignee: Mariposa Biotechnology, Inc., San Clemente, CA (US)

( * ) Notice: Subject to any disclaimer, the term of this patent is extended or adjusted under 35 U.S.C. 154(b) by 0 days.

(21) Appl. No.: 15/074,531

(22) Filed: Mar. 18, 2016

(65) Prior Publication Data

US 2016/0262374 A1      Sep. 15, 2016

Related U.S. Application Data

(62) Division of application No. 13/055,134, filed as application No. PCT/US2009/051428 on Jul. 22, 2009.

(60) Provisional application No. 61/116,255, filed on Nov. 19, 2008, provisional application No. 61/083,043, filed on Jul. 23, 2008.

(51) Int. Cl.
*A01N 1/02* (2006.01)
*C12N 5/075* (2010.01)

(52) U.S. Cl.
CPC ........... *A01N 1/0221* (2013.01); *A01N 1/0252* (2013.01)

(58) Field of Classification Search
None
See application file for complete search history.

(56) References Cited

U.S. PATENT DOCUMENTS

| 2006/0046243 | A1* | 3/2006 | Stachecki | ............ | A01N 1/02 435/1.3 |
| 2008/0113431 | A1* | 5/2008 | Diaz | ............... | A01N 1/0221 435/366 |
| 2008/0268492 | A1* | 10/2008 | Mullen | .............. | A01N 1/02 435/29 |

OTHER PUBLICATIONS

Fosas et al, Human Reproduction, 2003, vol. 18, No. 7, pp. 1417-1421.*
Office Action dated Aug. 1, 2016 from U.S. Appl. No. 13/055,134.

* cited by examiner

*Primary Examiner* — Allison Fox
(74) *Attorney, Agent, or Firm* — K. David Crockett, Esq.; Crockett & Crockett, PC

(57) ABSTRACT

An automated system and method of cryopreservation of oocytes, embryos, or blastocysts. The method entails delivering two or more solutions into a container holding oocytes, embryos, or blastocysts, and controlling the flow of the solutions to gradually change the concentration of cryoprotectants and dehydrating agents in the container to minimize shock to the oocytes, embryos or blastocysts.

10 Claims, 10 Drawing Sheets

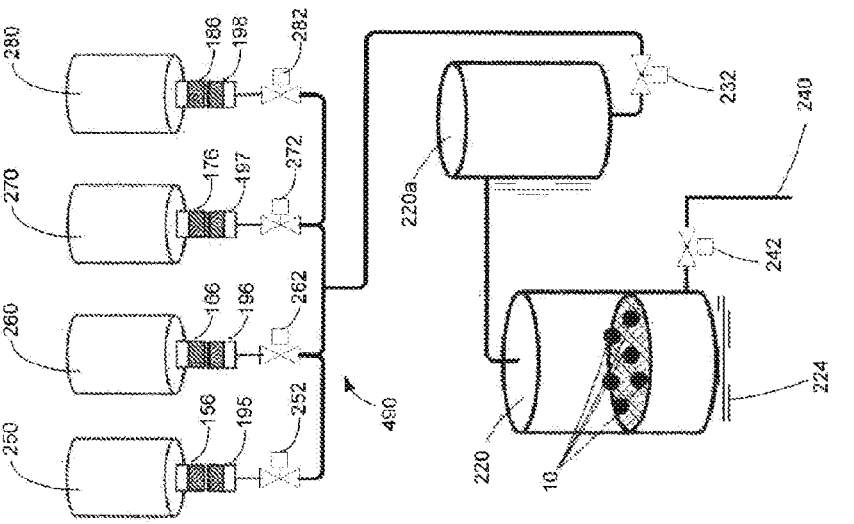
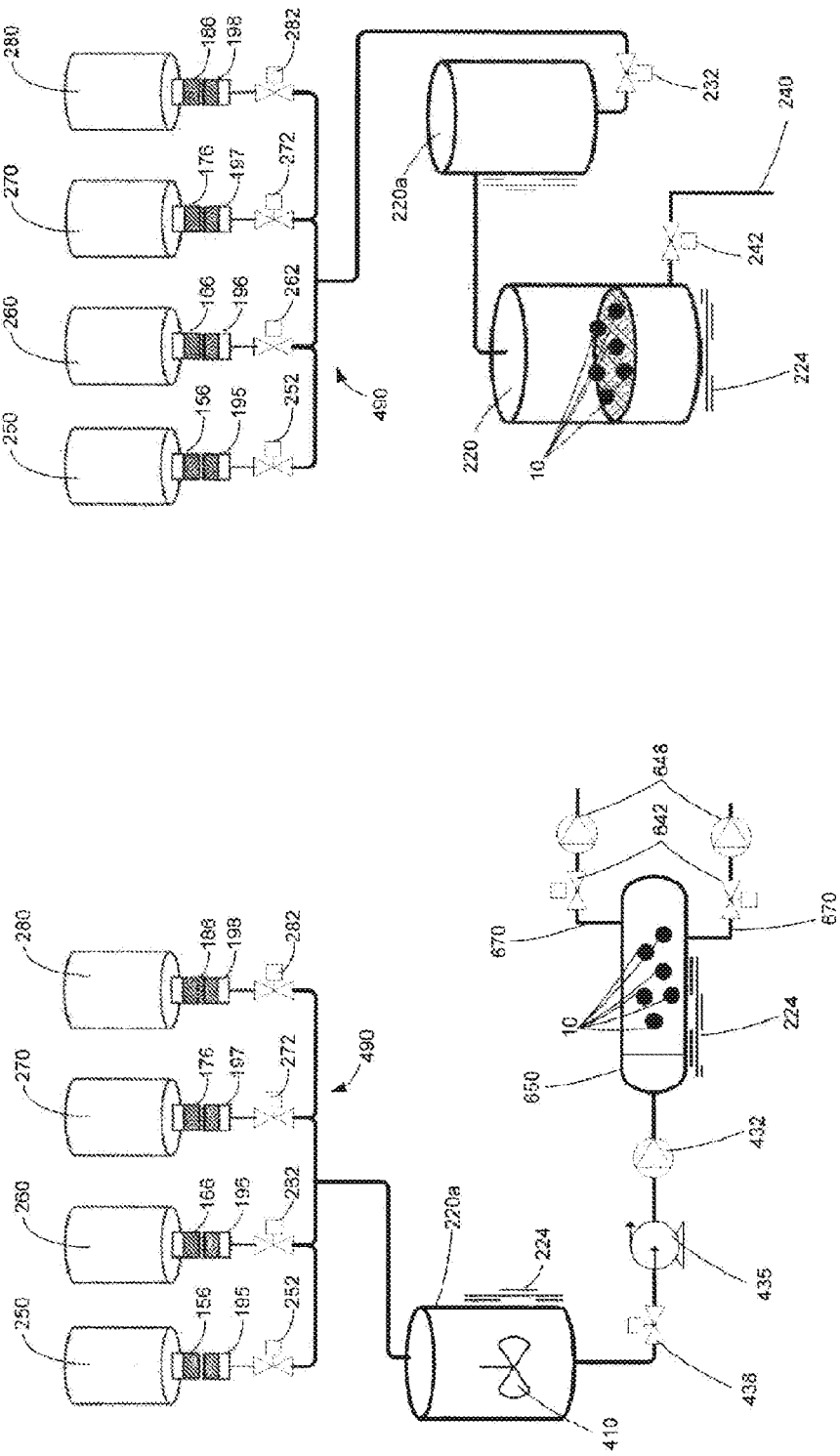

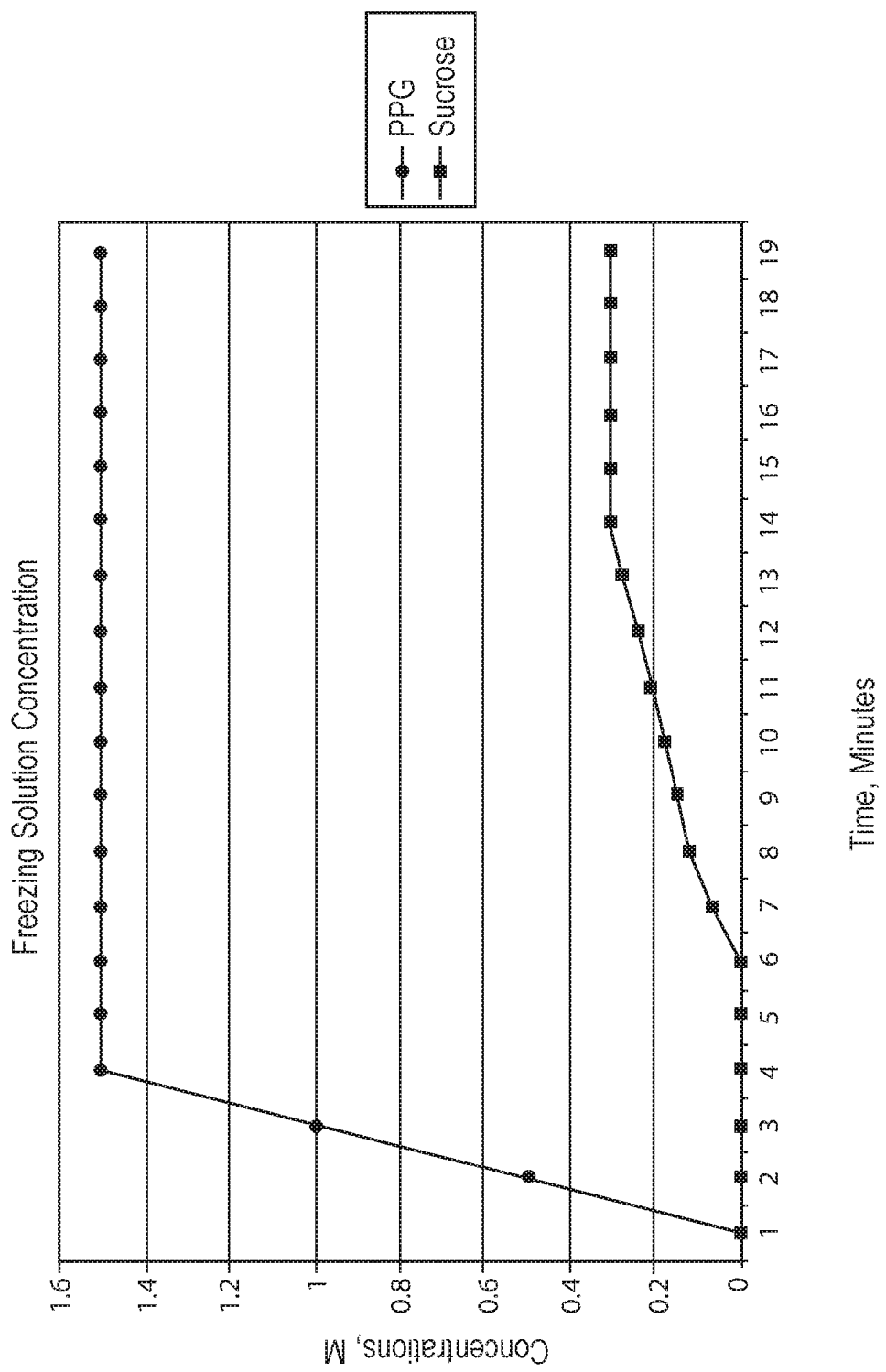

METHOD OF PREPARING OOCYTES, EMBRYOS, OR BLASTOCYSTS FOR CRYOPRESERVATION

This application is a divisional of U.S. application Ser. No. 13/055,134, filed May 12, 2011, pending, which is a national stage of PCT/US2009/051428 filed Jul. 22, 2009, which claims priority to U.S. Provisional Application 61/083,043, filed Jul. 23, 2008 and U.S. Provisional Application 61/116,255, filed Nov. 19, 2008.

FIELD OF THE INVENTION

The present invention relates generally to the field of cryopreservation. In particular, the present invention relates to systems and methods for providing automated change in the solution environment for the cryopreservation and/or reanimation of oocytes, embryos or blastocysts.

BACKGROUND OF THE INVENTION

This section is intended to provide a background or context to the invention that is recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

The ability to cryopreserve and then reanimate oocytes, embryos or blastocysts is desirable for many reasons. However, conventional techniques have proven difficult to reproduce in an effective, efficient and consistent manner. Such conventional techniques are typically labor-intensive, requiring substantial handling of the oocytes, embryos or blastocysts by a highly skilled human technician. For example, conventional cryopreservation of an oocyte requires that the technician manually move the oocytes from one location to another in the cryopreservation process, such as from incubation to washing solution to a cryoprotectant solution. Further, oocytes frequently incur structural damage during conventional cryopreservation techniques. For example, conventional manual movement of oocytes among cryopreservation solution baths can impart osmotic and thermal shock. For instance, formation of ice crystals within the oocyte can cause intracellular damage in the oocyte. Oocytes undergoing conventional cryopreservation techniques can also experience a loss of sphericity and undesirable changes in volume. Such effects may result in structural damage in addition to toxicity, thereby significantly diminishing the viability of the oocyte and ultimately reducing the probability of successful fertilization.

Human involvement and conventional preservation techniques greatly contribute to the lack of consistency in cryopreservation of oocytes, embryos or blastocysts and results in an undesirably low fertilization success rate. Therefore, it is desirable to provide a partially automated method and system for the repeatable and efficient cryopreservation and reanimation of oocytes, embryos or blastocysts that mitigate effects harmful to the viability of the oocyte, embryo or blastocyst, and thereby increasing the rate of successful fertilization.

SUMMARY OF THE INVENTION

Various embodiments of the present invention provide a method of cryopreservation and reanimation of oocytes, embryos or blastocysts. The method comprises positioning one or more oocytes, embryos or blastocysts in a processing container, the processing container being configured to allow fluid to flow into and out of the processing container; and flowing two or more fluids into and out of the processing container with the oocytes, embryos or blastocysts retained therein. In an embodiment, the method further comprises controlling the temperature of the fluid in the processing container according to predetermined requirements. The flowing of the fluids may be controlled by a central controller adapted to control one or more valves coupled to the processing container.

Embodiments also provide for an apparatus for cryopreservation and reanimation of oocytes, embryos or blastocysts comprises a processing container configured to hold oocytes, embryos or blastocysts therein, the processing container being further configured to allow fluid to flow into and out of the processing container; one or more reservoirs of fluids coupled to the processing container; and a central controller adapted to control the flow of fluids from the one or more reservoirs into the processing container.

Various embodiments also provide for a reservoir configured for dispensing fluid comprises a defined volume of fluid, the fluid including one or more components for cryopreserving and reanimating oocytes, embryos or blastocysts; a coupler configured to fluidically couple the reservoir to an apparatus for cryopreservation of oocytes, embryos or blastocysts; and electronic identification indicia representative of an authorized reservoir, wherein the electronic identification indicia is readable by the cryopreservation apparatus.

In other embodiments, the invention relates to methods and apparatus for the maturation of an egg in preparation for freezing as well as development of an embryo after fertilization. The above embodiments may be adapted to substantially simulate an in vivo environment of the egg and/or the embryo. Solution fluids may be directed into and out of the processing container containing one or more of an egg and/or a fertilized embryo. Solution delivery may be manipulated based on various parameters monitored over the development and/or maturation period.

In yet another embodiment, the invention relates to a central controller coupled to one or more valves configured to control flow of fluids into and out of a processing container configured to hold oocytes, embryos or blastocysts and coupled to a thermal controller. The central controller may be configured to (a) introduce an aqueous solution into the processing container containing the oocytes, embryos or blastocysts, the aqueous solution comprising a cryoprotectant maintained at a temperature of from about 20° to about 38° C. to replace at least a portion of intracytoplasmic water in the oocytes, embryos or blastocysts by the cryoprotectant; (b) replace the aqueous solution in the processing container with a first dehydrating/cryoprotecting solution comprising a cryoprotectant and a dehydrating agent maintained at a temperature of from about 20° to about 38° C. to remove additional intra-cytoplasmic water while introducing additional cryoprotectant into the cytoplasm; and (c) decrease the temperature of the dehydrating/cryoprotecting solution to a temperature of from about 22° to about 26° C. during a period of from about 3 to about 10 minutes.

Various embodiments of the present invention also relate to a computer program product, embodied on a computer-readable storage medium, for controlling one or more valves and/or pumps configured to control flow of fluids into and out of a processing container for oocytes, embryos or blastocysts and for controlling a thermal controller. The computer program product comprises (a) computer code for introducing an aqueous solution into the processing container containing the oocytes, embryos or blastocysts, the aqueous solution comprising a cryoprotectant maintained at a temperature of from about 33° to about 38° C. to replace at least a portion of intracytoplasmic water in the oocytes, embryos or blastocysts by the cryoprotectant; (b) computer code for replacing the aqueous solution in the processing container with a first dehydrating/cryoprotecting solution comprising a cryoprotectant and a dehydrating agent maintained at a temperature of from about 33° to about 38° C. to remove additional intra-cytoplasmic water while introducing additional cryoprotectant into the cytoplasm; and (c) computer code for decreasing the temperature of the dehydrating/cryoprotecting solution to a temperature of from about 22° to about 26° C. during a period of from about 3 to about 10 minutes.

These and other advantages and features of the invention, together with the organization and manner of operation thereof, will become apparent from the following detailed description when taken in conjunction with the accompanying drawings, wherein like elements have like numerals throughout the several drawings described below.

BRIEF DESCRIPTION OF THE DRAWINGS

FIG. 3A illustrates a cryopreservation and reanimation system according to another embodiment of the present invention;

FIG. 3B illustrates a cryopreservation and reanimation system according to yet another embodiment of the present invention;

FIG. 7 is a graphical representation of a solution concentration profile for a cryopreservation system in accordance with an embodiment of the present invention;

DETAILED DESCRIPTION OF VARIOUS EMBODIMENTS

Figure 1:
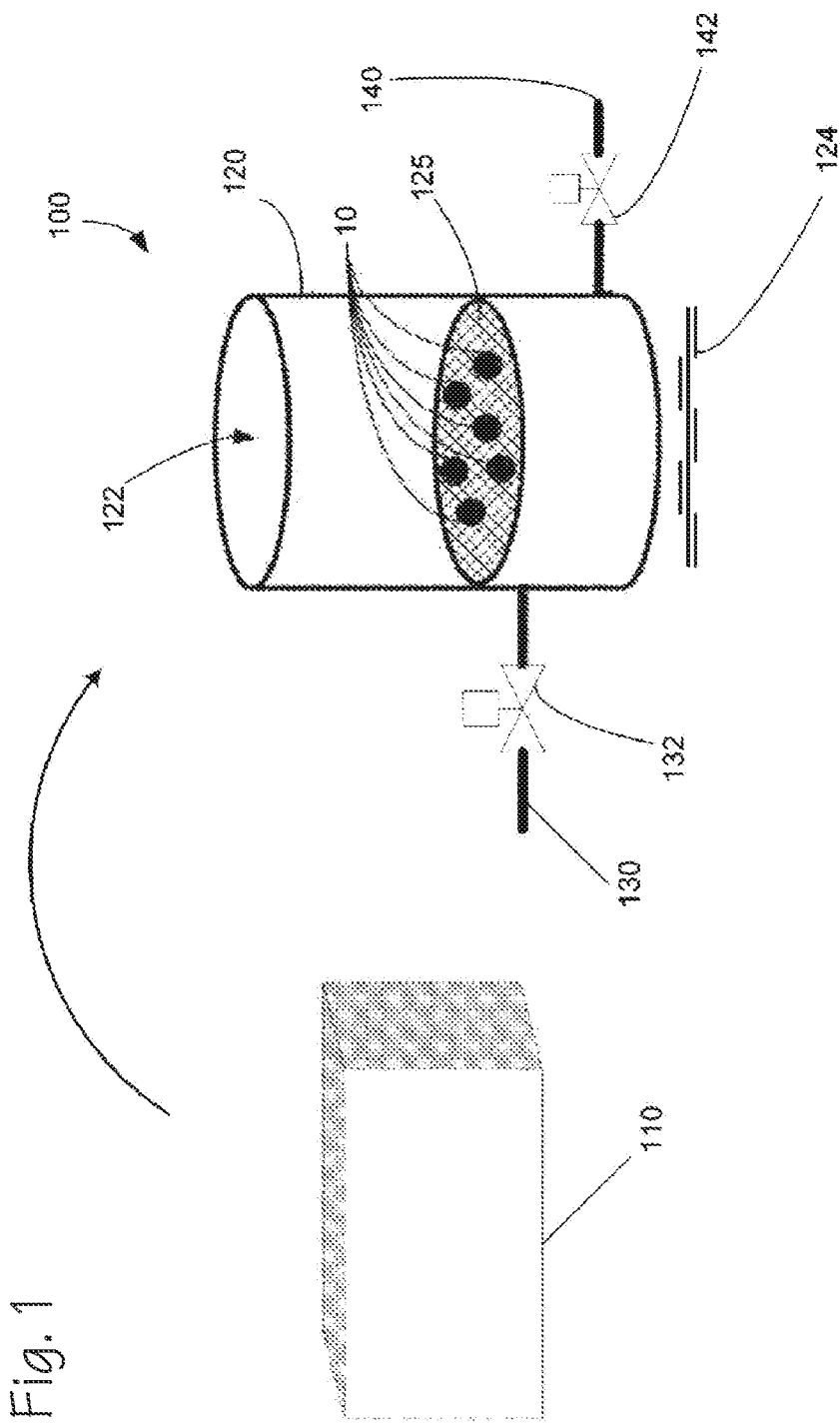
FIG. 1 illustrates a cryopreservation and reanimation system according to an embodiment of the present invention.

As used herein, the following definitions shall apply unless otherwise indicated.

The term "oocyte" refers to an unfertilized freshly harvested or mature oocyte and refers to both the singular and plural regardless of whether this term employs terms such as "a", "the" and the like. The freshly harvested means that the oocytes were harvested from the animal donor within 8 hours of initiation of the stabilization/cryopreservation process, preferably within about 4 hours of initiation of the stabilization/cryopreservation process, more preferably within about 1 hour of initiation of the stabilization/cryopreservation process, and even more preferably within about 0.1 hour of initiation of the stabilization/cryopreservation process The mature oocytes mean harvested oocytes which are graded on a maturation scale as "mature stage—MII." This scale further identifies harvested oocytes as "intermediate stage—(MI)" or "immature stage—(GV)."

The term "reanimated oocytes" refers to thawed oocytes which are capable of fertilization and embryo development.

The term "stabilized oocytes" refer to mature oocytes still retaining the cumulus mass (granulosa cells) which permit maturation of the oocyte by nutrient intake through gap junctions in the cumulus mass. The mature oocyte is characterized by formation of the meiotic spindle in conjunction with extrusion of the first polar body while maintaining the integrity/activity of the intracellular proteins.

The term "blastocyst" refers to a fertilized egg freshly harvested from about 5 days after fertilization up to implantation in the uterus and refers to both the singular and plural regardless of whether this term employs terms such as "a", "the" and the like. The term "freshly harvested" means that the blastocysts were harvested from the animal donor within about 8 hours of initiation of the stabilization/cryopreservation process, preferably within about 4 hours of initiation of the stabilization/cryopreservation process, more preferably within about 1 hour of initiation of the stabilization/cryopreservation process, and even more preferably within about 0.1 hour of initiation of the stabilization/cryopreservation process.

The term "reanimated blastocyst" refers to thawed blastocysts which are capable of embryo development.

The term "embryo" refers to a fertilized egg freshly harvested from between the time of first division to two cells to about 5 days after fertilization and refers to both the singular and plural regardless of whether this term employs terms such as "a", "the" and the like. The freshly harvested means that the embryos were harvested from the animal donor within about 8 hours of initiation of the stabilization/cryopreservation process, preferably within about 4 hours of initiation of the stabilization/cryopreservation process, more preferably within about 1 hour of initiation of the stabilization/cryopreservation process, and even more preferably within about 0.1 hour of initiation of the stabilization/cryopreservation process.

The term "reanimated embryos" refers to thawed embryos which are capable of further embryonic and fetal development.

In the following description, for purposes of explanation and not limitation, details and descriptions are set forth in order to provide a thorough understanding of the present invention. However, it will be apparent to those skilled in the art that the present invention can be practiced in other embodiments that depart from these details and descriptions.

Various processes for cryopreservation and reanimation of oocytes are conventionally known. One such process for cryopreserving freshly harvested mature animal oocytes comprises: incubating freshly harvested mature oocytes in one or more stabilization solutions maintained at a temperature of from about 33° to about 38° C. for a period of time sufficient to stabilize the oocytes to in vitro conditions, wherein when more than one stabilization solution is employed, each solution is different from each other. The stabilization solutions include, but are not limited to, those solutions wherein the freshly harvested mature oocyte is incubated after in vivo extraction and which permit the oocytes to equilibrate in its in vitro environment prior to initiation of the cryopreservation process. The stabilization solutions are intended to permit further maturation of the oocytes in vitro. Specifically, the stabilization solutions are designed to mimic the environment within the follicle from which the eggs were removed. The follicle supports ongoing processes of the oocyte maturation in vivo which are preferably duplicated when the oocytes are removed from the follicle and placed into the stabilization solution. The stabilization solution also provides nutrients for further meiotic development and supports metabolic processes continuing within the oocyte as well as supports the cell membrane. A further function of the stabilization solution is to remove biological wastes occurring from metabolism within the oocytes and to stabilize the intra-oocyte pH. The stabilization solution does not include any cryoprotectant, e.g., dimethyl sulfoxide (DMSO), propylene glycol, or the like.

Stabilization solutions include, by way of the example, Global® media (available from Life Global, IVF Online), Global® media supplemented with SSS (available from Irvine Scientific, Santa Ana, Calif., USA), human tubal solution (HTF—available from Irvine Scientific, Santa Ana, Calif., USA) optionally supplemented with SSS and/or an antibiotic (e.g., gentamicin) and modified HTF (HTF with HEPES (mHTF)—available from Life Global, IVF Online) optionally supplemented with SSS and/or an antibiotic (e.g., gentamicin), phosphate buffered saline (PBS), sodium depleted PBS (e.g., sodium hydrogen phosphate ($H_2NaPO_4$)) and the like.

Cryoprotectant is introduced into the stabilized mature oocyte by contacting the oocyte with an aqueous solution comprising a cryoprotectant maintained at a temperature of from about 33° to about 38° C. under conditions wherein at least a portion of the intracytoplasmic water is replaced by cryoprotectant. The cryoprotectant include, but are not limited to, a liquid which permeates across the cell wall of the animal oocyte typically by osmotic methods and which promotes survival and retention of viability of the oocyte during the process of cryopreserving as well as in the cryopreserved state. Suitable cryoprotectants are well known in the art and include, by way of example only, DMSO, ethylene glycol, propylene glycol (1,2-propanediol), glycerol, as well as mixtures of 2 or more of such cryoprotectants, and the like.

The oocyte is then transferred to at least a first dehydrating/cryoprotecting solution comprising a cryoprotectant and a dehydrating agent maintained at a temperature of from about 33° to about 38° C. under conditions sufficient to remove additional intra-cytoplasmic water while introducing additional cryoprotectant into the cytoplasm The temperature of the dehydrating/cryoprotecting solution is then decreased to about 22° to about 26° C. during a period of from about 3 to 10 minutes, and the oocyte is then transferred in the dehydrating/protecting solution into a container which is then sealed, and the oocytes are then cryopreserved. The dehydrating/cryoprotecting solution include, but are not limited to, a cryoprotecting solution as described above which further comprises an agent to facilitate dehydration of the intra-cytoplasmic water in the oocyte during cryopreservation Preferably, such agents do not osmotically traverse the cellular wall of the oocyte Dehydrating agents include, sucrose, dextrose, trehalose, lactose, raffinose, and the like.

Embodiments of the present invention provide systems and methods which allow for the automation of one or more of the steps of cryopreservation and reanimation techniques for oocytes, such as described above. Embodiments of the present invention are also adaptable for cryopreservation and reanimation of embryos and blastocysts. Embodiments of the present invention are particularly well suited for cryopreservation and reanimation of human oocytes, embryos, and blastocysts. The various exemplary embodiments will be described as and referred to as cryopreservation systems. However, it should be understood that the embodiments are not limited to cryopreservation but are also adapted for reanimation of oocytes, embryos and blastocysts. Additionally, the various embodiments may also be adapted for maturation of an egg in preparation for freezing as well as development of an embryo after fertilization.

Referring to FIG. 1, a cryopreservation system according to an embodiment of the present invention is illustrated. The cryopreservation system 100 includes an incubator 110 for incubation of freshly harvested mature oocytes, embryos or blastocysts 10. As noted above, the oocytes, embryos or blastocysts 10 may be incubated in one or more stabilization solutions maintained at a temperature of from about 33° to about 38° C. for a period of time sufficient to stabilize the oocytes, embryos or blastocysts 10 to in vitro conditions. Once the incubated oocytes, embryos or blastocysts 10 are stabilized, they are transported to a processing container 120.

The processing container 120 can be formed of a variety of materials, such as metals or plastics, for example. The processing container may be configured for efficient disassembly from the cryopreservation system 100 for sterilization. Alternatively, the processing container may be configured for single-use. The processing container 120 may be sized for specific uses and needs. In an embodiment, the processing container 120 has an internal volume 122 of about 0.0004 to about 0.02 ml. In another embodiment, the internal volume 122 is about 0.004 to about 0.008 ml. The internal volume 122 is configured to accommodate one or more oocytes, embryos or blastocysts 10 therein, along with a fluid solution. The oocytes, embryos or blastocysts 10 may be protected from other components of the processing container by a barrier. For example, the oocytes, embryos or blastocysts 10 can be separated from an inlet 130 and an outlet 140 of the processing container by a membrane 125 or another form of a barrier, generically illustrated in FIG. 1 by a dashed line. The membrane 125 is configured to retain the oocytes, embryos or blastocysts 10 within the processing container during processing, yet permit flow through of the processing solutions to allow for bathing of the oocytes, embryos or blastocysts 10. In an embodiment, the membrane 125 comprises a porous substrate with pores of about 5 μm to about 70 μm in diameter.

Figure 6A:
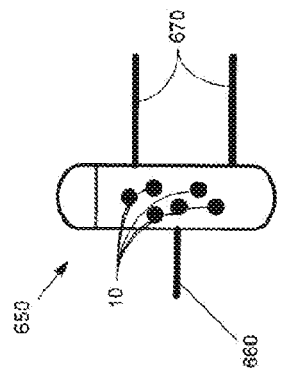
FIG. 6A illustrates an embodiment of an oocyte, embryo or blastocyst basket for use with the cryopreservation and reanimation systems of FIGS. 1, 2, 3A and 3B.

In another embodiment, the oocytes, embryos or blastocysts 10 are retained in a basket 600 configured to fit within the processing container 120, as depicted in FIG. 6A. The basket includes a plurality of pores 610 configured for flow through of the processing solutions but not greater than about 50 μm in diameter for retention of the oocytes, embryos or blastocysts 10 within the basket.

Figure 6B:
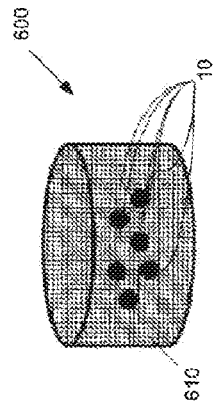
FIG. 6B illustrates another embodiment of an oocyte, embryo or blastocyst container for use with the cryopreservation and reanimation systems of FIGS. 1, 2, 3A and 3B.

In yet another embodiment, depicted in FIG. 6B, the oocytes, embryos or blastocysts 10 are loaded into a processing container 650 that is capable of being substantially sealed. The processing container 650 is configured with an inlet 660 and one or more outlets 670. The inlet 660 is configured for inflow of the processing solutions and the one or more outlets 670 are configured for outflow of the processing solutions. The inlet 660 and the one or more outlets 670 are further configured to retain the oocytes, embryos or blastocysts 10 within the processing container 650 during processing. In one configuration, the inlet 660 and the one or more outlets 670 are not greater than about 100 μm in diameter.

Figure 6C:
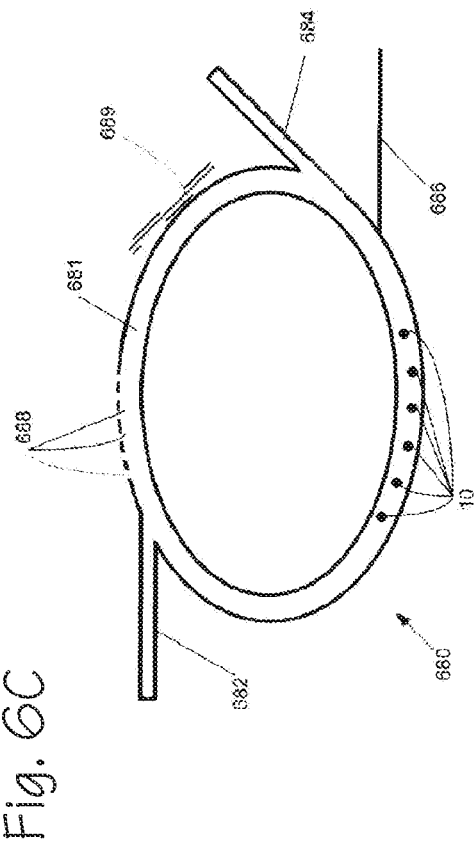
FIG. 6C illustrates yet another embodiment of an oocyte, embryo or blastocyst container for cryopreservation and reanimation of oocytes, embryos or blastocysts for use with the cryopreservation systems of FIGS. 1, 2, 3A and 3B.

In still another embodiment, depicted in FIG. 6C, the oocytes, embryos or blastocysts 10 enter a track 680. The track 680 comprises a hollow tube 681 forming a loop and configured with one or more ports. The loop formed by the hollow tube 681 is substantially circular in an embodiment and has a diameter of at least about 1 inch. The hollow tube 681 is sized to accommodate at least the normal maximum diameter of an oocyte, embryo or blastocyst 10 and a boundary layer of solution sufficient for cryopreservation of the oocyte, embryo or blastocyst 10. In an embodiment, the inner diameter of the hollow tube 681 is at least about 0.03 inch.

The oocytes, embryos or blastocysts 10 enter the track 680 from a port 682. In an embodiment, the track 680 is configured for clockwise flow of the solution fluids and the oocytes, embryos or blastocysts 10 about the loop formed by the hollow tube 681. The port 682 is disposed on the track 680 such that the oocytes, embryos or blastocysts 10 are substantially prevented from exiting through the port 682 while clockwise fluid flow is maintained within the hollow tube 681. The solution fluids enter the track 680 through a solution port 684. The solution port 684 is disposed on the track 680 to encourage clockwise flow about the track 680 in response to entry of the solutions into the hollow tube 681. The solution port 684 is similarly disposed on the track 680 to prevent entry of the oocytes, embryos or blastocysts 10. The solution port 684 is coupled to a plurality of reservoirs 150, 160, 170, and 180 or a single reservoir 300/301, illustrated in FIGS. 2 and 4A/4B respectively. Excess solution escapes from the track 680 through a plurality of slits 688 disposed on the outer surface of the hollow tube 681 and substantially normal to the flow direction within the track 680. The slits 688 are configured to prevent escape or capture of the oocytes, embryos or blastocysts 10 within the hollow tube 681. In an embodiment, the slits 688 are not greater than about 50 μm in width. The track 680 optionally includes a gas port 686 disposed substantially opposite the port 682. The track 680 may further include a temperature controller 689 for control of the process temperature.

The oocytes, embryos or blastocysts 10 are carried around the loop formed by the hollow tube 681 by a substantially continuous flow of cryoprotectant solutions until the cryopreservation process is complete. Upon process completion, suction is provided at the port 682 to retrieve the oocytes, embryos or blastocysts 10 from the track 680. The gas port 686 supplies a positive pressure to facilitate retrieval of the oocytes, embryos or blastocysts 10 from the track 680 through the port 682.

As illustrated in FIG. 1, the processing container 120 is configured to allow fluid to flow into and out of the internal volume 122. In the illustrated embodiment the flow of fluid into and out of the internal volume 122 is controlled by valves in the inlet 130 and the outlet 140, such as an inlet valve 132 and an outlet valve 142. The inlet valve 132 and outlet valve 142 are sized to accommodate the flow of fluid as required for the processing of the oocytes, embryos or blastocysts 10. The processing container 120 optionally includes a baffle 126 to improve solution mixing within the processing container.

The processing container 120 is also provided with a thermal controller 124 configured to control the temperature of the fluid in the internal volume 122. Various configurations may be used to control fluid temperature. For example, the solutions may be held at room temperature, and at least a portion of the solution is heated and cooled, as necessary, to achieve the desired process solution temperature. In an embodiment, the process temperature range is from about 20° to about 37° C. Alternatively, the solutions may be maintained at about the maximum of the process temperature range, and at least a portion of the solution is cooled, as necessary, to achieve the desired process solution temperature. In yet another embodiment, the solutions may be maintained at about the minimum of the process temperature range, and at least a portion of the solution is heated, as necessary, to achieve the desired process solution temperature. In the embodiment illustrated in FIGS. 1 and 2, the thermal controller 124 is coupled to a wall of the processing container 120. In other embodiments, a thermal controller 124 may be coupled to the inlet 130 to control the temperature of the fluid entering the internal volume 122 of the processing container 120. In still other embodiments, one or more of the thermal controllers 124 may couple to the plurality of reservoirs 150, 160, 170, and 180. Still further, the thermal controller 124 may be implemented in any of numerous other manners known in the art to allow thermal control of the fluid in the internal volume 122.

Figure 2:
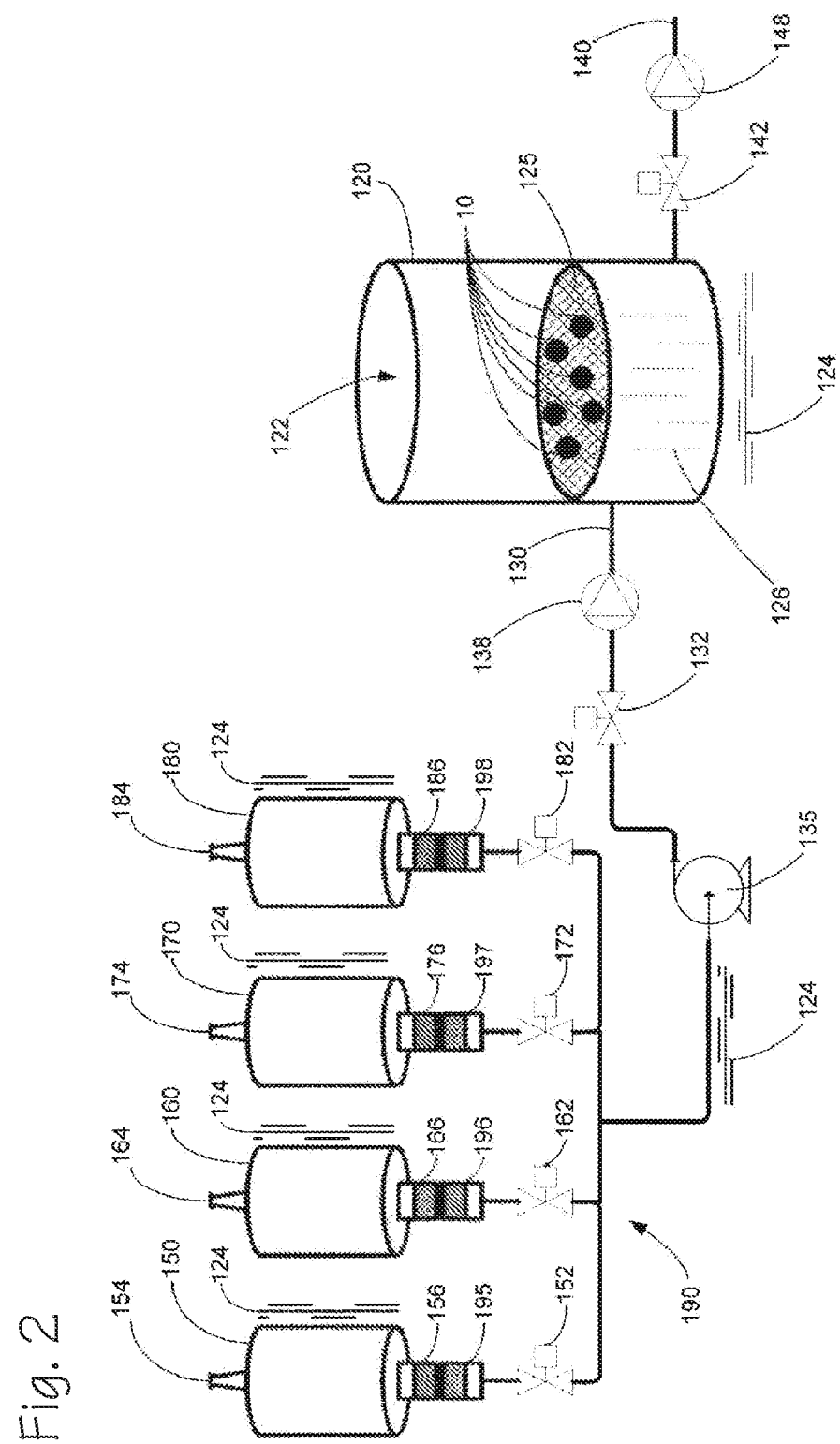
FIG. 2 illustrates the cryopreservation and reanimation system of FIG. 1 with additional features.

The cryopreservation system may include one or more solution reservoirs fluidically coupled to the processing container 120. Referring to FIG. 2, the cryopreservation system of FIG. 1 is illustrated with additional features. In the illustrated embodiment, the cryopreservation system includes the plurality of reservoirs 150, 160, 170, and 180 fluidically coupled to the processing container 120. The plurality of reservoirs 150, 160, 170, and 180 hold one or more solutions appropriate for the cryopreservation or reanimation of the oocytes, embryos or blastocysts 10 within the processing container 120. In the illustrated embodiment, the reservoir 150 holds a volume of solution I; the reservoir 160 holds a volume of solution II; the reservoir 170 holds a volume of solution III; and the reservoir 180 holds a volume of solution IV. The plurality of reservoirs 150, 160, 170, and 180 are configured to hold a volume of solution sufficient to process one or more batches of oocytes, embryos or blastocysts 10 within the processing container 120. In an embodiment, the plurality of reservoirs 150, 160, 170, and 180 have a substantially equal volume of about 3 ml. In another embodiment, the plurality of reservoirs 150, 160, 170, and 180 are of various volumes, sized in relation to the volume of their respective solutions for processing the oocytes, embryos or blastocysts 10.

The composition of the solutions I, II, III, and IV is configured to provide the desired sequence of solutions for cryopreservation or reanimation of the oocytes, embryos or blastocysts 10 according to, for example, the cryopreservation process described above. In this regard, in an embodiment, Solution I includes an aqueous stabilizing solution comprising a modified human tubal fluid ("mHTF") and a synthetic serum substitutes ("SSS") as known in the art.

Solution II comprises an aqueous solution of mHTF, SSS, and a cryoprotectant configured to replace at least a portion of the intracytoplasmic water in the oocytes, embryos or blastocysts 10 with cryoprotectant. Solution III comprises a first dehydrating/cryoprotecting solution including a cryoprotectant and a dehydrating agent configured to remove additional intra-cytoplasmic water from the oocytes, embryos or blastocysts 10 while introducing additional cryoprotectant into the cytoplasm. Solution IV comprises a second dehydrating/cryoprotecting solution including a cryoprotectant and a dehydrating agent configured to remove additional intra-cytoplasmic water from the oocytes, embryos or blastocysts 10 while introducing additional cryoprotectant into the cytoplasm. The system is readily adapted for use with alternative solutions or solution components. For example, in an embodiment, SSS is eliminated from the solutions. In another embodiment, solutions comprising saline, HTF, mHTF, and an aqueous solution including choline chloride may be used. In addition, other solutions and solution components may be used with the various embodiments to achieve the desired cryopreservation or reanimation of oocytes, embryos, and/or blastocysts.

In another embodiment, each of the plurality of reservoirs may contain one or more of the solution components of the solutions I, II, III, and IV. For example, the embodiment of FIG. 2 illustrates the plurality of reservoirs 150, 160, 170, and 180. In this embodiment, each of the four reservoirs contains a volume of an individual solution component or mixture of selected solution components at an appropriate concentration corresponding to the process described above or other cryopreservation process. For example in an embodiment, the reservoir 150 includes a volume of mHTF; the reservoir 160 includes a volume of SSS; the reservoir 170 includes a volume of cryoprotectant; and the reservoir 180 includes a volume of dehydrating solution. Combinations of the components with each other or other components may be included in the plurality of reservoirs 150, 160, 170, and 180. Again, the system is readily adapted for use with alternative solutions or solution components as earlier described. An appropriate volume of the solution components from the plurality of reservoirs 150, 160, 170, and 180 are released through the plurality of corresponding valves 152, 162, 172 and 182. The solution components mix to form the solutions I, II, III, and IV, or other combinations thereof, corresponding to the different stages of the cryopreservation process. The manifold 190 is configured to enhance the mixing of the solution components to form adequately homogenous solutions prior to release of the solutions into the processing container 120.

The plurality of reservoirs 150, 160, 170, and 180 are fluidically coupled to the manifold 190 with a plurality of corresponding couplers 156, 166, 176, and 186. The plurality of corresponding couplers 156, 166, 176, and 186 are configured to couple to a plurality of corresponding manifold connections 195, 196, 197, and 198. The corresponding plurality of couplers 156, 166, 176, and 186 may be uniquely configured to couple to only one of the plurality of corresponding manifold connections 195, 196, 197, and 198. The unique connections may be accomplished through any one of a number of techniques known in the art, such as, but not limited to, connection diameter, internal and/or external engagement features, connection thread pitch, connection thread direction, keyed connectors, or any combination thereof. Unique coupling connections ensure correct assembly of the plurality of reservoirs 150, 160, 170, and 180 to the manifold 190 and delivery of the appropriate solutions to the processing container 120.

In an embodiment, each of the plurality of reservoirs 150, 160, 170, and 180 comprise a reservoir surface forming a substantially closed vessel. The reservoir surface may be of a rigid, semi-rigid, or deformable material that is non-reactive with the solutions or solution components retained therein. The reservoir surface may be formed into a generally cylindrical shape or another form suitable for storing and dispensing the solutions. The reservoir surface includes at least one opening whereby the solution or solution component exits the respective reservoir through the corresponding plurality of couplers 156, 166, 176, and 186. The reservoir surface may be constructed with an integral opening or the opening may be formed when the respective reservoir is coupled to the cryopreservation system 100. In an embodiment, the opening and/or reservoir surface may form all of or a portion of the corresponding valves 152, 162, 172 and 182.

In an embodiment, the plurality of reservoirs 150, 160, 170, and 180 are configured for limited use. For example, limited volumes of the solutions or solution components may be provided sufficient only to process a predefined number of oocyte, embryo or blastocyst batches. In an embodiment, the volumes of solutions or solution components are configured for processing a single batch of oocytes, embryos or blastocysts Once a single-use reservoir is depleted, the reservoir is decoupled from the cryopreservation system 100 and a replacement reservoir, filled with the appropriate solution or solution component, is attached. Alternatively, the plurality of reservoirs 150, 160, 170, and 180 may be configured for limited use based on other parameters.

For instance, to ensure optimal performance, the plurality of reservoirs 150, 160, 170, and 180 may be configured with electronic data indicative of a date, an age, or an expiration date of the solution or solution component readable by the cryopreservation system 100. The cryopreservation system 100 may deny use if it detects an expired reservoir in certain embodiments. Similarly, the plurality of reservoirs 150, 160, 170, and 180 may be configured with electronic identification data indicative of the solution or the solution component readable by the cryopreservation system 100. The cryopreservation system 100 may deny use in various embodiments if it detects a reservoir containing an improper or incompatible solution or solution component.

The electronic data and electronic identification data may be associated with or stored on the plurality of reservoirs 150, 160, 170, and 180 in a reservoir storage structure using any of the variety of storage structures known in the art. For instance, an EPROM, non-volatile memory, magnetic strip, RFID, or other storage structure can be associated with each of the plurality of reservoirs the 150, 160, 170, and 180 to store the data. In embodiments where two or more reservoirs are coupled, a portion of the reservoir storage structure may be associated with each of the reservoirs. The cryopreservation system 100 is provided with a corresponding system to detect and read the data from the reservoir storage structures. The cryopreservation system 100 reads the data from the reservoir storage structure and compares the data to existing or downloaded data within the cryopreservation system 100 or external data.

In an embodiment, the electronic identification indicia may be used to ensure that the plurality of reservoirs 150, 160, 170, and 180 are coupled to the proper plurality of corresponding manifold connections 195, 196, 197, and 198. The cryopreservation system 100 may deny use if it detects an improperly coupled reservoir or a reservoir that is coupled an incorrect one of the plurality of corresponding manifold connections 195, 196, 197, and 198. In another embodiment, the cryopreservation system 100 is dynamically adaptable such that the configuration of the plurality of reservoirs 150, 160, 170, and 180 to the of corresponding manifold connections 195, 196, 197, and 198 is irrelevant. The cryopreservation system 100 detects the electronic identification indicia of the plurality of reservoirs 150, 160, 170, and 180 and configures operation accordingly. In this particular embodiment, it is unnecessary to provide unique coupling configurations for the plurality of corresponding manifold connections 195, 196, 197, and 198 and the corresponding plurality of couplers 156, 166, 176, and 186.

In another embodiment, to prevent use of uncertified solutions or counterfeit solutions, the plurality of reservoirs 150, 160, 170, and 180 may include electronic identification indicia readable by the cryopreservation system 100 and indicative of an authorized reservoir. The cryopreservation system 100 may deny use if it is unable to verify the integrity of the reservoir, the solution, or solution component via the electronic identification indicia or other indicia. The electronic identification indicia or other indicia may be encoded or encrypted to prevent unauthorized replication of the indicia. The cryopreservation system 100 may deny operation if it fails to detect an authorized reservoir among the plurality of reservoirs 150, 160, 170, and 180 based on the electronic identification supplied by the reservoir. The electronic identification indicia may further be configured to lapse upon depletion of a reservoir. Still further, the electronic identification indicia of the plurality of reservoirs 150, 160, 170, and 180 may be automatically or manually associated with one or more particular batches of oocytes, embryos or blastocysts processed in the cryopreservation system 100 and stored in a data record for subsequent recall or analysis. The plurality of reservoirs 150, 160, 170, and 180 may be disposable following use or may be configured for authorized reuse If the reservoir is reusable, upon depletion, the reservoir is returned to a solution provider for authorized replenishment of solution and renewal of the electronic identification indicia.

The contents of the plurality of reservoirs 150, 160, 170, and 180 are directed to the internal volume 122 of the processing container 120 through a manifold 190. The flow of the solutions I, II, III, and IV or solution components to the internal volume 122 may be controlled through one or more valves. As illustrated in the embodiment of FIG. 2, delivery of the solution or solution component from the plurality of reservoirs 150, 160, 170, and 180 may be regulated through a plurality of corresponding valves 152, 162, 172, and 182, respectively. An inlet valve 132, downstream of the corresponding valves 152, 162, 172, and 182 may further be provided to control flow into the processing container 120. The plurality of corresponding valves 152, 162, 172, and 182 may comprise one or more of any of several manual or automatic valve types or structures known in the art capable of restricting fluid flow. In the illustrated embodiment, the corresponding valves 152, 162, 172, and 182 are positioned between the corresponding manifold connections 195, 196, 197, and 198 and the processing container 120. In another embodiment, the corresponding valves 152, 162, 172, and 182 are positioned between the plurality of reservoirs 150, 160, 170, and 180 and the corresponding couplers 156, 166, 176, and 186. In yet another embodiment, a portion of the reservoir surface comprises the corresponding valves 152, 162, 172, and 182.

The solutions or solution components are delivered from their respective reservoirs to the processing container 120 by one or more fluid delivery techniques known in the art. For example, the cryopreservation system 100 may be configured for gravity feed of the solutions into the processing container 120. In another embodiment, a pump 135 may be installed between the plurality of reservoirs 150, 160, 170, and 180 and the processing container 120 for delivery of the solutions to the processing container 120. Alternatively, or in addition to the pump 135, a pump may be associated with each of the plurality of reservoirs 150, 160, 170, and 180 to deliver the respective solutions to the manifold 190.

In another embodiment, air and/or inert gas is used alone, or in combination with one or more pumps, to dispense the solutions to the processing container 120. For example, the plurality of reservoirs 150, 160, 170, and 180 may be configured to include a corresponding gas inlet 154, 164, 174, and 184. The cryopreservation system 100 supplies pressurized gas to the plurality of reservoirs 150, 160, 170, and 180 via gas lines coupled to the respective corresponding gas inlets 154, 164, 174, and 184. Supply of the individual solutions or solution components to the processing container 120 is regulated by the gas flow to each of the plurality of reservoirs 150, 160, 170, and 180. In this configuration, the plurality of corresponding valves 152, 162, 172, and 182 need only be responsive to pressure changes within the plurality of reservoirs 150, 160, 170, and 180 supplied by the gas. Each of the corresponding gas inlets 154, 164, 174, and 184 may be uniquely configured such that only a specific gas line, corresponding to one of the plurality of reservoirs 150, 160, 170, and 180, may be coupled. Provision of unique configurations eliminates human error when installing new reservoirs. The regulation of gas flow may be fully automated based on a defined cryopreservation process sequence or in response to cryopreservation process parameters monitored during the course of the process. Use of an inert gas to deliver the solutions has the added benefit, in an at least partially closed cryopreservation system, of regulating the cryopreservation process pressure, which may advantageously improve inflow of cryoprotectants across the oocyte, embryo or blastocyst cell boundary. Further, conducting the cryopreservation process an inert atmosphere reduces the opportunity for contaminants to enter the cryopreservation system 100.

Figure 4A:
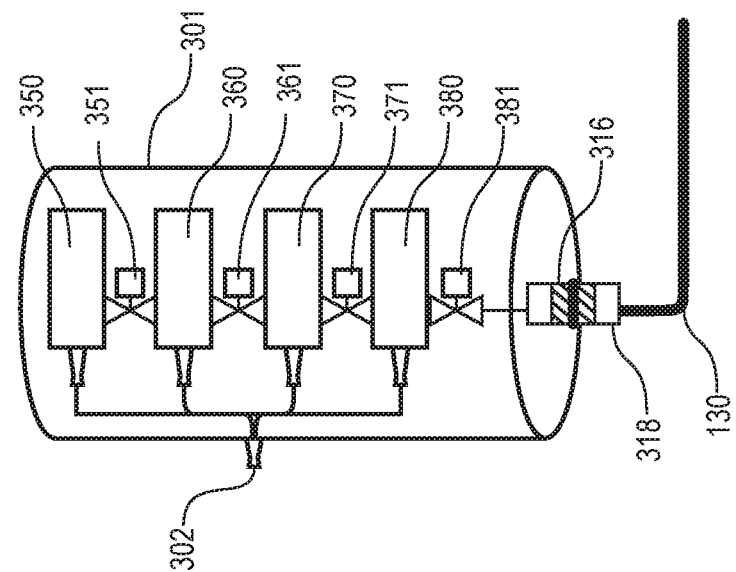
FIG. 4A illustrates an embodiment of a reservoir for use with the cryopreservation and reanimation systems illustrated in FIGS. 1, 2, 3A, and 3B.
Figure 4B:
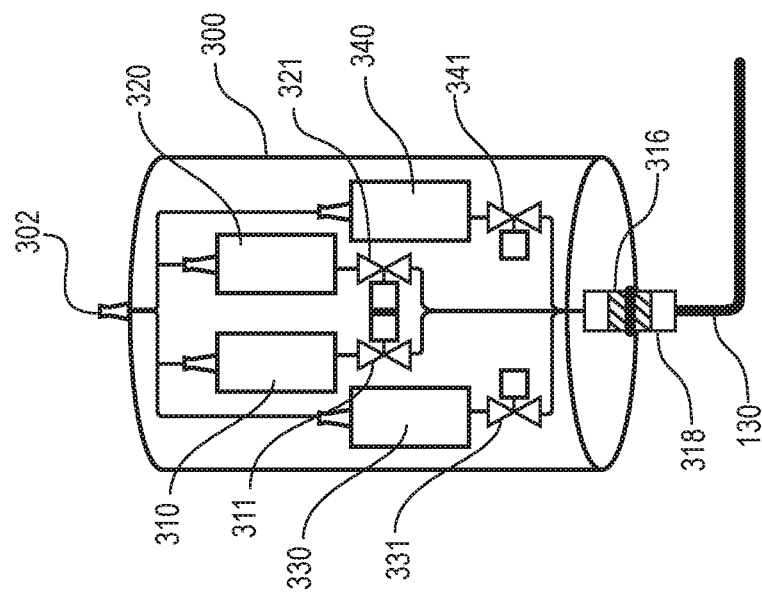
FIG. 4B illustrates another embodiment of a reservoir for use with the cryopreservation and reanimation systems illustrated in FIGS. 1, 2, 3A, and 3B.

Other configurations of the solution reservoirs of the cryopreservation system 100 can also be constructed. Referring to FIGS. 4A and 4B, embodiments of single reservoir systems are depicted. In the illustrated embodiments, a single reservoir containing each of the solutions or solution components is coupled to the processing container 120. In these embodiments, individual solutions or solution components are maintained in sub-compartments within the single reservoir.

In the embodiment depicted in FIG. 4A, a single reservoir 300 houses a plurality of sub-compartments 310, 320, 330, and 340. Each of the plurality of sub-compartments 310, 320, 330, and 340 hold a volume of solution or solution component for use in the cryopreservation of the oocytes, embryos or blastocysts 10 within the processing container 120. The single reservoir 301 includes a reservoir coupler 316 configured to couple to an inlet connection 318 of the cryopreservation system 100. A reservoir manifold 305 fluidically interconnects the plurality of sub-compartments 310, 320, 330, and 340 with the reservoir coupler 316. The reservoir manifold 305 may include a plurality of corresponding valves 311, 321, 331, and 341 associated with the plurality of the sub-compartments 310, 320, 330, and 340. The plurality of corresponding valves 311, 321, 331, and 341 may be selected from any of a number of valve types known in the art for controlling or restricting flow. The illustrated embodiment may be configured for use with the process solutions or the solution components.

In the embodiment depicted in FIG. 4B, a single reservoir 301 houses a plurality of interconnected sub-compartments 350, 360, 370, and 380. Each of the plurality of sub-compartments 350, 360, 370, and 380 hold a volume of solution for the cryopreservation of the oocytes, embryos or blastocysts 10 within the processing container 120. The single reservoir 301 includes a reservoir coupler 316 configured to couple to an inlet connection 318 of the cryopreservation system 100. A plurality of corresponding valves 351, 361, 371, and 381 control fluid flow out of the plurality of sub-compartments 350, 360, 370, and 380. The plurality of corresponding valves 351, 361, 371, and 381 can be selected from any of a number of valve types known in the art for restricting flow. The illustrated embodiment is primarily configured for use with ordered process solutions. For example, the sub-compartment 350 contains a volume of solution I; the sub-compartment 360 contains a volume of solution II; the sub-compartment 370 contains a volume of solution III; and the sub-compartment 380 contains a volume of solution IV. In this manner, the single reservoir 301 is generally applicable for single-use, wherein a single oocyte, embryo or blastocyst batch may be processed with the single reservoir 301. A new single reservoir 301 is coupled to the cryopreservation system 100 to process each subsequent oocyte, embryo or blastocyst batch.

The solutions or solution components are delivered from the single reservoirs 300/301 to the processing container 120 by one or more fluid delivery techniques known in the art. For example, the cryopreservation system may be configured for gravity feed of the solutions into the processing container 120. Additionally, a pump 135 may be installed between the single reservoirs 300/301 and the processing container 120 for delivery of the solutions to the processing container 120.

Still further, air and/or inert gas may be used alone, or in combination with one or more pumps, to dispense the solutions to the processing container 120. For example, gas may be supplied to each the plurality of sub-compartments 310, 320, 330, and 340 through gas inlet 302. In an embodiment, the gas inlet 302 is configured to provide individually controllable gas streams to each of the plurality of sub-compartments 310, 320, 330, and 340. The gas streams are regulated by the cryopreservation system 100 in response to a defined process and/or monitored preservation process parameters. In this configuration, the plurality of corresponding valves 311, 321, 331, and 341 need only be responsive to pressure changes within the plurality of sub-compartments 310, 320, 330, and 340 supplied via the gas inlet 302. This configuration may also be adapted for use with the single reservoir 301.

In another embodiment, the gas inlet 302 is configured to provide a single regulated gas stream to all of the sub-compartments. In this configuration, the plurality of corresponding valves 351, 361, 371, and 381 may be configured to be progressively responsive to increasing gas flow received by the plurality of sub-compartments 350, 360, 370, and 380 from the gas inlet 302. For example, the valve 381 is responsive to a pressure $P_1$ supplied to the plurality of sub-compartments 350, 360, 370, and 380 such that a volume of solution I contained in sub-compartment 380 is released to the inlet 130. The valve 371 is responsive to a pressure $P_2$, which is greater than $P_1$ thereby releasing a volume of solution II. The valve 361 is responsive to a pressure $P_3$, which is greater than $P_2$, thereby releasing a volume of solution III. The valve 351 is responsive to a pressure $P_4$, which is greater than $P_3$, thereby releasing a volume of solution IV Regulation of gas flow may be fully automated based on a defined cryopreservation process sequence or in response to cryopreservation process parameters monitored during the course of the process.

The single reservoir 300/301 provides a convenient configuration for replenishment of the cryoprotectant solutions of the cryopreservation system 100 and minimizes the opportunity of error during replenishment. Further, the single reservoir 300/301 may be configured for single use or a limited number of uses such as by providing volumes of solutions or solution components sufficient only for the preservation of one, or a predefined number, of oocyte, embryo or blastocyst batches. Further, the single reservoir 300/301 may include electronic identification indicia readable by the cryopreservation system 100 and indicative of an authorized reservoir. The electronic identification indicia may be configured to lapse upon depletion of the single reservoir 300/301. The cryopreservation system 100 may deny use of the reservoir 300/301 if it fails to detect a signal indicative of an authorized reservoir. Still further, the electronic identification indicia of the single reservoir 300/301 may be automatically or manually associated with a particular batch of processed oocytes, embryos or blastocysts and stored in a data record for subsequent recall or analysis. The single reservoir 300/301 may also be configured for authorized reuse. Upon depletion of the single reservoir 300/301, it is returned to a solution provider for authorized replenishment with cryoprotectant and renewal of the electronic identification indicia.

In the above embodiments, systems have been described having a plurality of reservoirs or sub-compartments comprising four reservoirs or sub-compartments. However, other embodiments having either greater or fewer reservoirs or sub-compartments may be constructed. For example, one or more of the solutions or the solution components may be combined in one or more of the plurality of reservoirs or in one or more of the plurality of sub-compartments. Combining the solutions or solution components thereby reduces the total number of reservoirs coupled to the processing container 120 or reducing the total number of sub-compartments within the single reservoir 300/301. Still other embodiments can be constructed for use with cryopreservation processes employing additional solutions or solution components where more than four reservoirs or sub-compartments are desired. Other solution components may include permeation enhancers configured to enhance the outflow of aqueous components out of and/or the inflow of cryoprotectants into the oocyte, embryo or blastocyst.

In the above described embodiments, continuous temperature control may be provided during the cryopreservation or reanimation process to mitigate thermal shock and prevent formation of intracellular ice crystal in the oocytes, embryos or blastocysts 10. The thermal controller 124 adjusts the temperature of the solution as it enters or after it has entered the internal volume 122. In another embodiment, the temperature of the solutions or solution components within the plurality of the reservoirs 150, 160, 170, and 180 is at least partly controlled within the reservoirs by thermal controllers 124 so that when the solution enters the internal volume 122 of the processing container 120, the solution temperature is not significantly different from the desired temperature for the cryopreservation or reanimation process. In another embodiment, the desired temperature of the various solutions is at least partially attained by a temperature controller 124 coupled to the manifold 190. In yet another embodiment, a combination thermal controller is implemented whereby multiple thermal controllers are used. For example, the thermal controller 124 maintains the solution temperature in the solution reservoirs within a desired range and, more precisely, regulates the temperature of the solution in the processing container 120. Continuous temperature control of the processing solutions reduces thermal stress imparted to the oocyte, embryo or blastocyst while in the cryopreservation system 100 and improves viability of the processed oocytes, embryos or blastocysts.

The above described embodiments of the cryopreservation system may also be adapted for use in various other contexts by using alternative solutions and/or solution components. For example, the above described embodiments may be used for maturation of an egg in preparation for freezing as well as development of an embryo after fertilization. The cryopreservation system may be adapted for processing of a single embryo or egg or configured to simultaneously process a plurality of embryos and or eggs in a single or multiple processing containers. For example, multiple processing containers may be coupled to a manifold to deliver solutions and/or solution components. In one such embodiment, solutions and/or solution components may be used to substantially simulate an in vivo environment of the egg and/or the embryo, e.g. traversal of a fallopian tube. Further, solution control may also be adapted to substantially simulate the in vivo environment. Solution fluids may be directed into and out of the processing container containing one or more of an egg and/or a fertilized embryo.

In one embodiment, the solution fluids are delivered to the processing container to substantially simulate a relative velocity of the one or more eggs and/or fertilized embryos from about 2 cm/day to about 1 cm/hour. In yet another embodiment, delivery of the solution fluids to the processing container may be controlled at least in part on the concentration of dissolved oxygen of the solution environment. In still another embodiment, delivery of solution fluids, including change, addition, and deletion of solutions or solution components, to the process container may be controlled over the course of the maturation and/or development period.

In yet another embodiment, imaging and or detection capability may be used to visualize and monitor the viability of the one or more eggs and/or embryos over the course of the process. Various imaging techniques and measurement systems known in the art, such as ultrasound and optical imaging systems, may be used to assess integrity, growth and well being of the one or more eggs and/or embryos. The collected information may also be used to control and/or modify solution delivery to the processing container.

Figure 5:
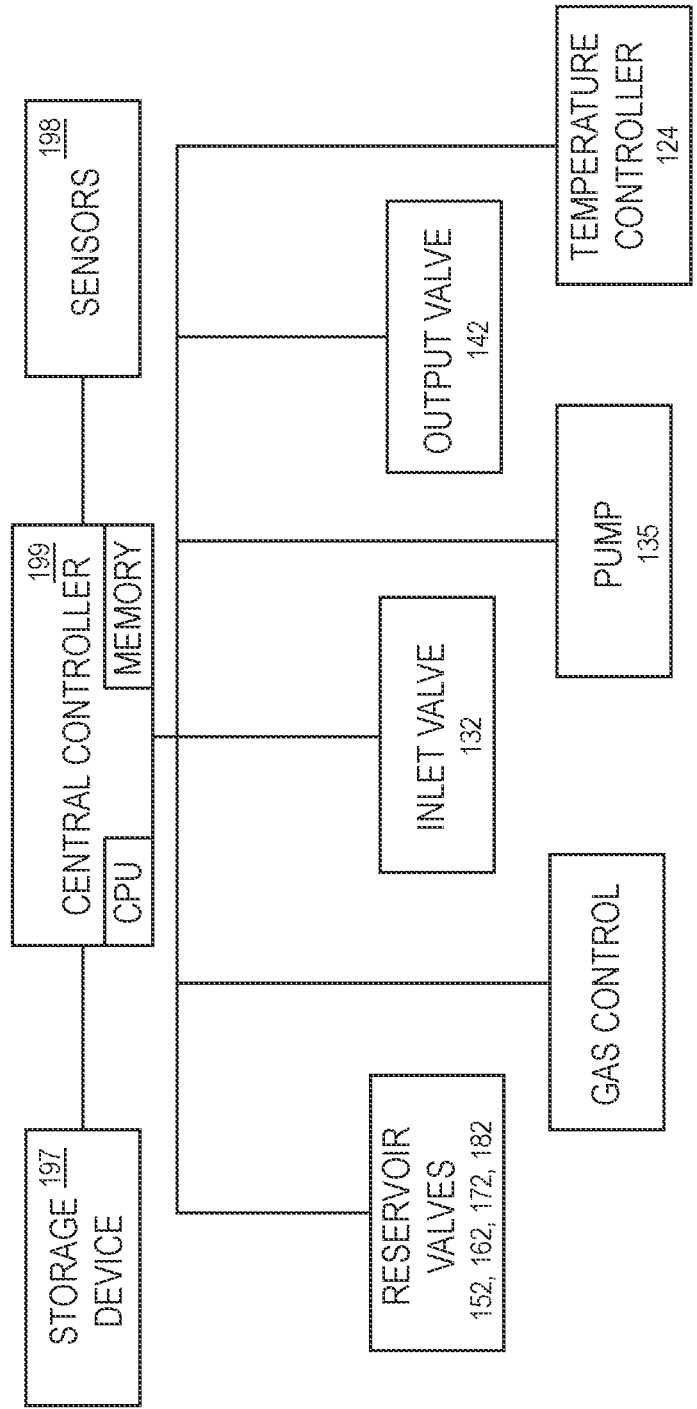
FIG. 5 schematically illustrates a control arrangement for use with the cryopreservation and reanimation system of FIGS. 1 and 2 in accordance with an embodiment of the present invention.

Referring to FIG. 5, a control arrangement for use with the cryopreservation system of FIGS. 1, 2, 3A and 3B is schematically illustrated. The control arrangement comprises a central controller 199 coupled to various components of the cryopreservation system. The central controller 199 may be implemented as a central processing unit (CPU) or other such device. In an embodiment, the central controller 199 includes a processor and a memory unit. The memory unit includes computer code for executing the various steps of a method to effect the cryopreservation of the oocytes, embryos or blastocysts.

As schematically illustrated in FIG. 5, the central controller 199 is coupled to various components of the cryopreservation system, such as the inlet valve 132, the outlet valve 142 and the plurality of corresponding valves 152, 162, 172, 182 associated with each of the solution reservoirs of FIG. 2. The central controller 199 is also coupled to the temperature controller 124. Thus, the central controller 199 is able to control operation of the cryopreservation system by controlling the contents and conditions of the internal volume 122 of the processing container 120 in which the oocytes, embryos or blastocysts 10 are located.

The central controller 199 may be adapted to execute computer code for automatically performing a method to effect a cryopreservation or reanimation process by, for example, opening and closing the various valves and controlling the thermal control unit. Further, the central controller 199 may be configured to receive signals from one or more sensors 198 which may be positioned in or on the processing container 120 and in or on the various other structures comprising the cryopreservation system 100. The sensors 198 provide the central controller 199 with such information as the temperature, pressure, pH, and composition of the fluid in the internal volume 122 of the processing container 120. The sensors 198 may also provide the central controller 199 with the temperature of solution within the inlet 130, the outlet 140, and the plurality of reservoirs 150, 160, 170, and 180. The sensors 198 may further provide the central controller 199 with volumetric flow into and out of the processing container 120. In an embodiment, the inlet 130 is configured with an inlet flow meter 138 responsive to solution flow rate into the processing container 120. Similarly, the outlet 140 is configured with an outlet flow meter 148 responsive to solution flow rate out of the processing container 120. The central controller 199 is configured to process data received from the inlet flow meter 138 and the outlet flow meter 148 to assess volumetric change of the oocytes, embryos or blastocysts 10 during processing. For instance, the flow rate of the processing solution through the membrane 125 changes in response to the change in volume of the oocytes, embryos or blastocysts 10 during the cryopreservation process. The central controller 199 monitors the change in solution flow rate and may apply the information to control the cryopreservation process. The flow rate data may further be stored in the memory unit and associated with a particular oocyte, embryo or blastocyst batch for subsequent retrieval and processing indicative of oocyte, embryo or blastocyst viability.

The one or more sensors 198 may also measure the structural state of the oocytes, embryos or blastocysts 10 within the processing container 120. For example, a sensor 198 may be configured to measure sphericity of the oocytes, embryos or blastocysts 10 throughout the cryopreservation process. Sphericity is a measure of the roundness of the oocyte, embryo or blastocyst 10 and may be defined by the ratio of the surface area of a sphere, having a volume equal to the oocyte, embryo or blastocyst volume, to the surface area of the oocyte, embryo or blastocyst. Sphericity may also be approximated by circularity of the oocyte, embryo or blastocyst. Volume and surface area of the oocyte, embryo or blastocyst 10 can be determined from measurement systems known in the art such as ultrasound and optical imaging systems. The central controller 199 monitors data indicative of the sphericity of the oocytes, embryos or blastocysts 10 during processing and may apply the information to control the cryopreservation process. The sphericity data may further be stored in the memory unit and associated with a particular oocyte, embryo or blastocyst for subsequent retrieval and processing indicative of oocyte, embryo or blastocyst viability. For example, prior to fertilization, sphericity data for a plurality of oocytes may be consulted to aid the selection of likely fertilization candidates. Factors which may be utilized in calculating the composite score include, but are not limited to, volume change, sphericity, morphology of the oocyte and zona pelucida separately, analysis of the cell wall, and for oocytes specifically, a measure of the spindle, which may be performed, for example, with an OOSIGHT™ optical instrument from Cambridge Research & Instrumentation Inc. (CRI) of Woburn, Mass.

In an embodiment, a storage device 197 is coupled to the central controller 199. The storage device 197 is configured to store information received from the central controller 199 including information received from the sensors 198. The storage device 197 may collocated with the central processor. In another embodiment, the storage device 197 may be located remotely. Where the storage device 197 is remotely located, it may be adapted to store information from one or more cryopreservation systems 100. The storage device 197 may further be configured to accept and store information indicative of the oocytes, embryos or blastocysts processed in the cryopreservation system 100 such as identification information. The storage device 197 is capable of associating the oocyte, embryo or blastocyst information with the information received from the central controller 199. The storage device 197 may further be configured to accept and store external information. The information stored in the storage device 197 is retrievable for processing and analysis. In an embodiment, information regarding oocytes, embryos or blastocysts processed in the cryopreservation system is retrieved for assessment of viability to select a subset of oocytes, embryos or blastocysts for reanimation from a population of available oocytes, embryos or blastocysts. For instance, information related to the processing parameters, oocyte, embryo or blastocyst volume and sphericity, and imagery of one or more oocytes, embryos or blastocysts is retrieved and assessed to assist in isolating a subset of oocytes, embryos or blastocysts. The system may also generate a composite score indicative of the overall quality of the oocyte, embryo or blastocyst for ranking and selection of candidates.

The operation of the cryopreservation system 100 may be controlled in various manners in accordance with a desired cryopreservation or reanimation process. For example, in an embodiment, the central controller 199 effects sequential flowing of the solutions into the processing container 120. In this regard, the central controller 199 may control the valves and or gas flow such that the processing container 120 is first filled with Solution I and, after a predetermined time, the processing container 120 is emptied. The process may be repeated with each of the other solutions.

In another embodiment, the fluid environment of the oocytes, embryos or blastocysts is gradually altered to minimize shock to the oocytes, embryos or blastocysts. In this regard, the central controller 199 may first fill the processing container 120, 220, 600, 650, or 680 with a first solution. After a predetermined time, the first solution may be gradually removed while a second solution is supplied to the processing container 120. Other solutions may be gradually added or removed in accordance with a desired process parameters. Similarly, if solution components are used, the various solution components may be dispensed to achieve a high degree of control of the solution composition. Addition of the solutions or solution components may be fully automated and based on a predefined solution protocol. The predefined solution protocol may optionally be modified during processing in response to information received from the sensors 198 and processed by the central controller 199. By controlling the inflow of the individual solutions and or solution components into and the outflow from the processing container 120, the oocytes, embryos or blastocysts are exposed to a continuously changing concentration of cryoprotectant and dehydrating components over the course of the cryopreservation process. The continuous change in concentrations may further be combined with continuous control of the solution temperature. The process parameters of the cryopreservation system 100 are thereby optimized for rapid removal of aqueous components from the oocytes, embryos or blastocysts 10 and replacement with cryoprotectants.

Referring to FIGS. 3A and 3B, cryopreservation systems according to another embodiment of the present invention are illustrated. The cryopreservation systems illustrated in FIGS. 3A and 3B are similar to that illustrated in FIG. 2 and described above, but include an intermediate mixing container 220a. Thus, the cryopreservation systems of FIGS. 3A and 3B include a processing container 220 or 650 configured to house the oocytes, embryos or blastocysts 10 therein. Solutions I, II, III, and IV or the solution components are directed through a manifold 490 into the intermediate mixing container 220a from the plurality of reservoirs 250, 260, 270, and 280. The plurality of reservoirs 250, 260, 270, and 280 are coupled to manifold 490 as described above with the corresponding coupling connections. Alternatively, the single reservoir 300/301 may used in place of the plurality of reservoirs 250, 260, 270, and 280 and coupled to the manifold 490 with a single coupler. As noted above, the flow of the solutions or solution components is controlled by corresponding valves 252, 262, 272, and 282, respectively. Alternatively, as described above, flow of the solutions or solution components may be controlled via gas supplied to the plurality of reservoirs 250, 260, 270, and 280, or the sub-compartments of the single reservoirs 300/301.

In the cryopreservation systems illustrated in FIGS. 3A, and 3B, the fluid provided to the processing container 220/650 is mixed (and conditioned, if necessary) prior to exposing the oocytes, embryos, or blastocysts to the fluid. Thus, drastic changes to the fluid environment of the oocytes, embryos, or blastocysts are avoided. The solutions I, II, III, and IV or the solution components are allowed to mix in the intermediate mixing container 220a, and the mixed fluid is directed to the processing container 220 or 650 In the embodiment illustrated in FIG. 3A, the fluids are mixed with an impellor mixer 410. Alternative mixing structures, including a magnetic stirring bar, an integrated baffle, or other mixing structure known in the art can be substituted or used in combination with the impellor mixer 410.

Flow out of the intermediate mixing container 220a is regulated by an intermediate valve 438 and/or an intermediate pump 435. The intermediate valve 438 and the intermediate pump 435 are controllable by the cryopreservation system 100. The inlet 430 may include a flow meter 432 responsive to the solution flow rate into the processing container 650. Alternatively, as described above, the processing container 120 may be used in place of the processing container 650. A thermal controller 224 configured to control the temperature of the fluid in the intermediate mixing container 220a is optionally included. Similarly, the processing container 120/650 may be configured with a temperature controller 624 to control the temperature therein.

Fluid is directed out of the processing container 650 through one or more outlets 670 and out flow is controlled by one or more corresponding valves 648. The one or more corresponding valves 648 are controllable by the cryopreservation system 100. Flow rate out of the processing container 670 and through the one or more outlets 670 is monitored by one or more corresponding flow meters 642.

In the embodiment illustrated in FIG. 3B, flow of the mixed fluid from the intermediate mixing container 220a to the processing container 220 is achieved by allowing fluid to overflow from the intermediate mixing container 220a into the processing container 220. The inlet valve 232 controls the flow of the solutions into the intermediate mixing container 220a. Fluid is directed out of the processing container 220 through an outlet 240 and out flow is controlled by an outlet valve 242. Further, a thermal controller 224 is provided to control the temperature of the fluid in one or both of the intermediate mixing container 220a and the processing container 220.

Figure 8:
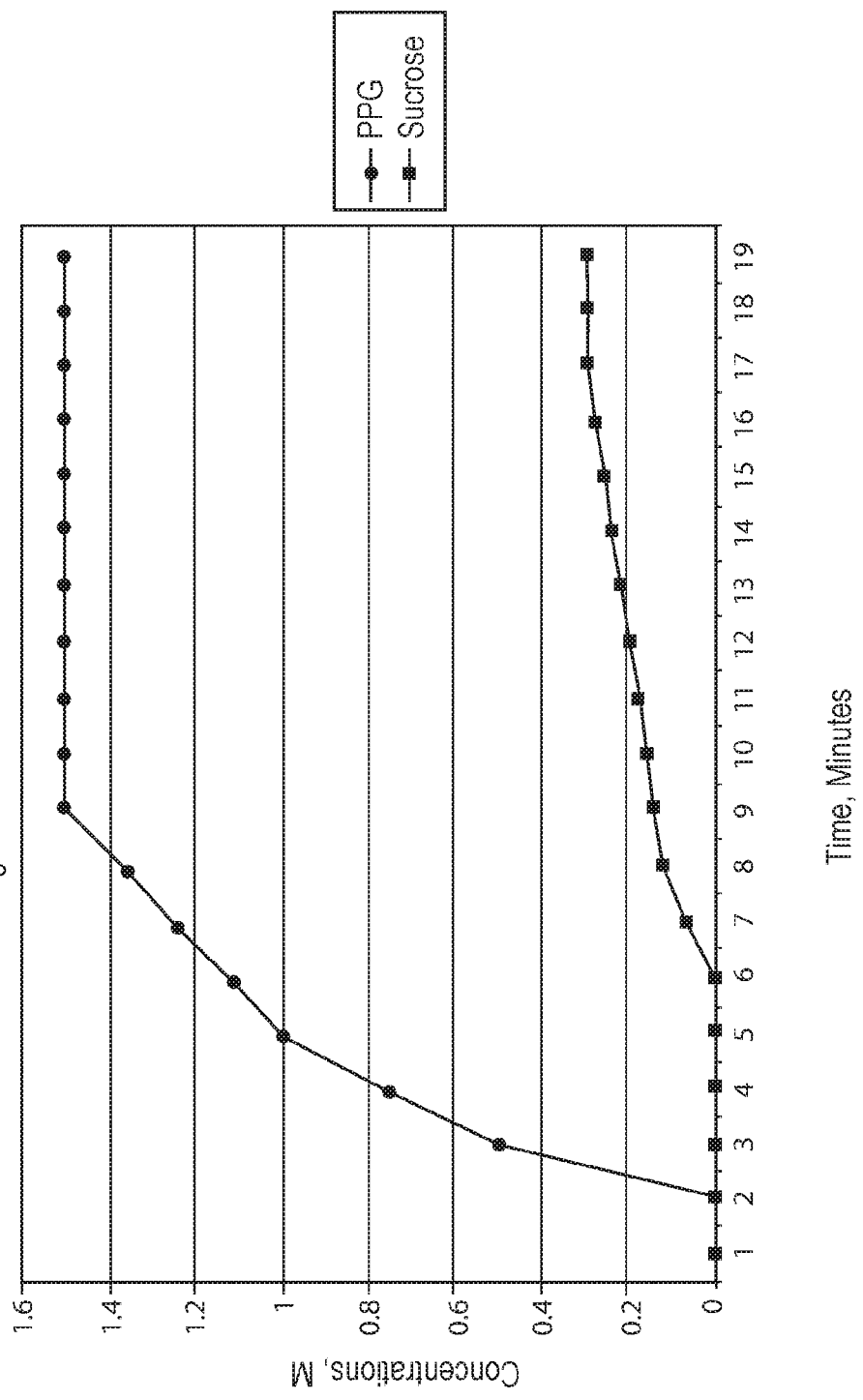
FIG. 8 is a graphical representation of another solution concentration profile for a cryopreservation system in accordance with an embodiment of the present invention.
Figure 9:
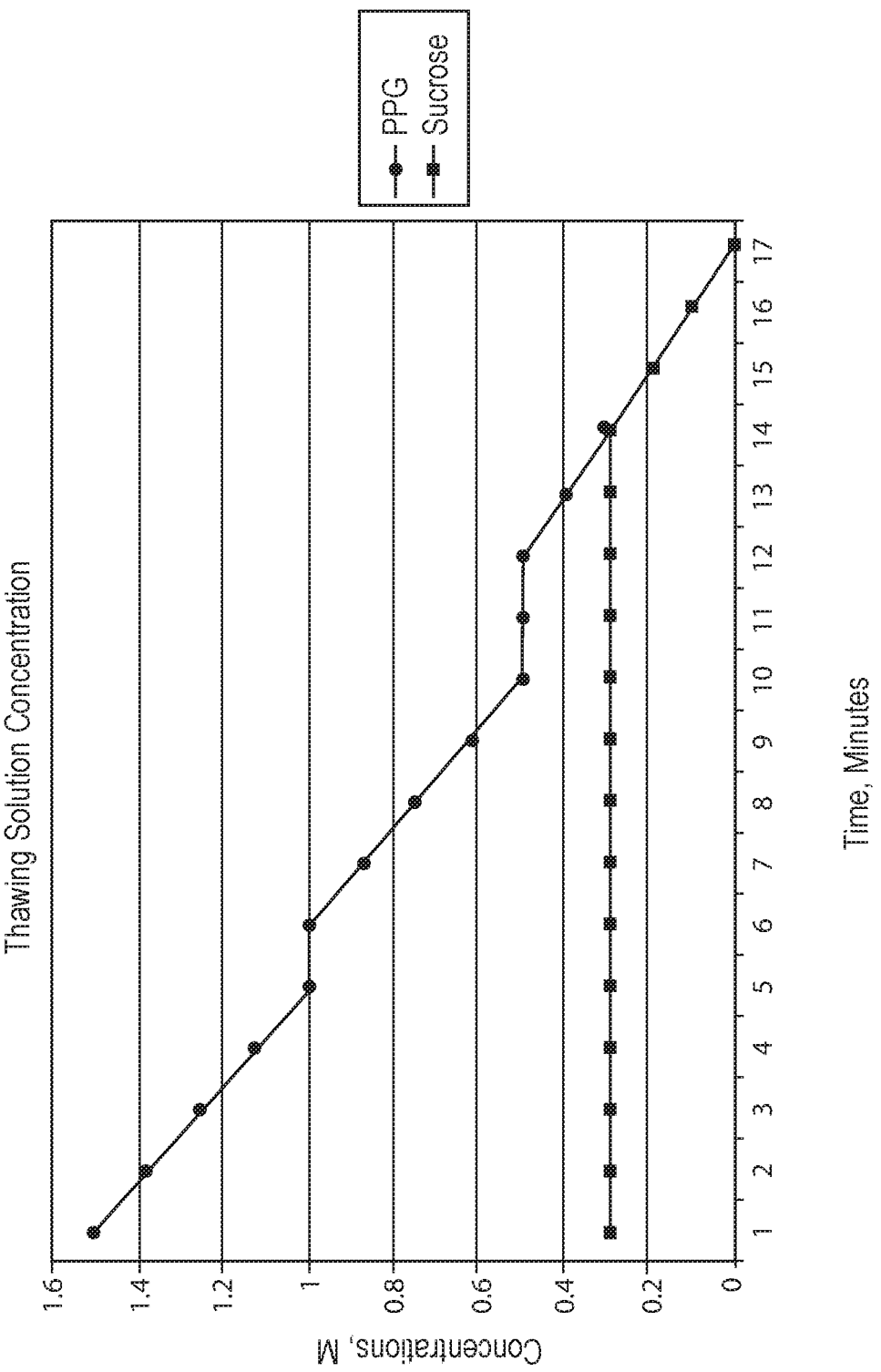
FIG. 9 is a graphical representation of a solution concentration profile for a reanimation system in accordance with an embodiment of the present invention.
Figure 10:
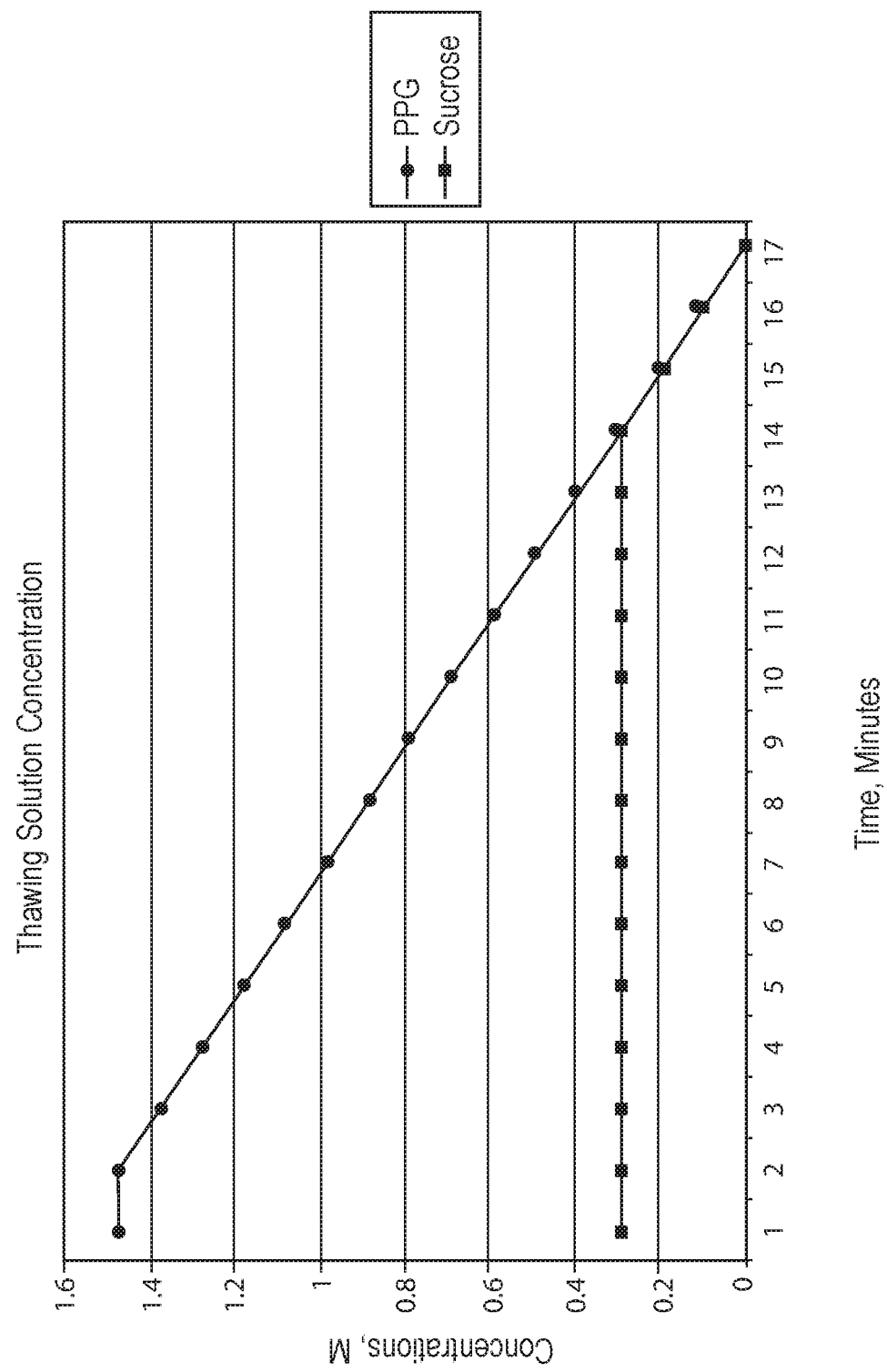
FIG. 10 is a graphical representation of another solution concentration profile for a reanimation system in accordance with an embodiment of the present invention.

FIGS. 7 and 8 illustrate exemplary solution concentration profiles for preservation processes that may be carried out with a cryopreservation system in accordance with an embodiment of the present invention. FIGS. 9 and 10 illustrate exemplary solution concentration profiles for reanimation processes that may be carried out with a cryopreservation system in accordance with an embodiment of the present invention. With reference to FIGS. 7-10, concentrations of cryoprotectant and dehydrant components are illustrated in relation to process time. In FIGS. 7-10, concentrations of propylene glycol and sucrose are illustrated by way of example. However, additional embodiments may encompass different concentration profiles and or different or additional components. For preparation for cryopreservation, the method may include steps in which the concentration of the cryoprotectant components is increased from about 0.0 M to about 1.5 M, and wherein the concentration of the dehydrating components of the fluid flowing into the processing container is increased from about 0.0 M to about 0.3 M. For reanimation, the method may include steps in which the concentration of the cryoprotectant components of the two or more fluids flowing into the processing container is decreased, and wherein a concentration of the dehydrating components of the two or more fluids flowing into the processing container is decreased. For reanimation, the method may include steps in which the concentration of the cryoprotectant components is decreased from about 1.5 M to about 0.0 M, and wherein the concentration of the dehydrating components of the fluid flowing into the processing container is decreased from about 0.3 M to about 0.0 M.

The methods and systems presented herein have been described for the cryopreservation of oocytes, embryos or blastocysts. However, one skilled in the art will appreciate that the above systems and methods are adaptable to the reanimation of oocytes, embryos, and blastocysts cryopreserved through the described methods or by other cryopreservation methods known in the art.

Various embodiments described herein are described in the general context of method steps or processes, which may be implemented in an embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc.

Embodiments of the present invention may be implemented in software, hardware, application logic or a combination of software, hardware and application logic. The software, application logic and/or hardware may reside, for example, on a chipset, a memory device or a processor.

While particular embodiments of the present invention have been disclosed, it is to be understood that various different modifications and combinations are possible and are contemplated within the true spirit and scope of the appended claims. There is no intention, therefore, of limitations to the exact abstract and disclosure herein presented. The features of the embodiments described herein may be combined in all possible combinations of methods, apparatus, modules, systems, and computer program products.

The invention claimed is:

1. A method of preparing oocytes for cryopreservation, said method comprising:
    positioning one or more oocytes in a container; and
    flowing a first solution comprising a cryoprotectant over the oocytes by delivering the first solution into the container and removing the first solution from the container, for a first time period;
    while delivering the first solution into the container, initiating flow of a second solution comprising a dehydrating agent into the container;
    wherein the step of initiating flow of the second solution is initiated while some of the first solution is in the processing container, and accomplished to gradually increase the concentration of the dehydrating agent in the container.

2. The method of claim 1, wherein the concentration of the cryoprotectant in the first solution is increased from about 0.0 M to about 1.5 M during the first period.

3. The method of claim 1, wherein the concentration of the dehydrating components in the second solution is increased from about 0.0 M to about 0.3 M during a second time period following the first time period.

4. The method of claim 2, wherein the concentration of the dehydrating components in the second solution is increased from about 0.0 M to about 0.3 M during a second time period following the first time period.

5. The method of claim 1 wherein the cryoprotectant comprises DMSO, ethylene glycol, propylene glycol, or glycerol, alone or in combination.

6. The method of claim 5 wherein the dehydrating agent comprises sucrose, dextrose, trehalose, lactose, or raffinose, alone or in combination.

7. The method of claim 1, further comprising the step of:
    prior to delivering the first solution comprising a cryoprotectant into the container, delivering a stabilizing solution into the container, and thereafter delivering the first solution, during the first time period, to gradually increase the concentration of cryoprotectant in the container over the first time period.

8. The method of claim 1 wherein the dehydrating agent comprises sucrose, dextrose, trehalose, lactose, or raffinose, alone or in combination.

9. The method of claim 8, further comprising the step of:
    prior to delivering the first solution comprising a cryoprotectant into the container, delivering a stabilizing solution into the container, and thereafter delivering the first solution, during the first time period, to gradually increase the concentration of cryoprotectant in the container over the first time period.

10. The method of claim 9 wherein the cryoprotectant comprises DMSO, ethylene glycol, propylene glycol, or glycerol, alone or in combination.

* * * * *